US00PP19509P3

(12) United States Plant Patent
Takeuchi

(10) Patent No.: US PP19,509 P3
(45) Date of Patent: Dec. 2, 2008

(54) HYBRID TEA ROSE PLANT NAMED 'KEIHABURU'

(50) Latin Name: *Rosa hybrida*
Varietal Denomination: KEIhaburu

(75) Inventor: Shunsuke Takeuchi, Chiba-Ken (JP)

(73) Assignee: Keisei Rose Nurseries, Inc., Tokyo (JP)

( * ) Notice: Subject to any disclaimer, the term of this patent is extended or adjusted under 35 U.S.C. 154(b) by 0 days.

(21) Appl. No.: 11/499,254

(22) Filed: Aug. 3, 2006

(65) Prior Publication Data

US 2007/0039079 P1 Feb. 15, 2007

(30) Foreign Application Priority Data

Aug. 10, 2005 (JP) ..... 17636

(51) Int. Cl.
*A01H 5/00* (2006.01)

(52) U.S. Cl. ..... Plt./137

(58) Field of Classification Search ..... Plt./137
See application file for complete search history.

*Primary Examiner*—Anne Marie Grunberg
*Assistant Examiner*—S. B. McCormick-Ewoldt
(74) *Attorney, Agent, or Firm*—Klarquist Sparkman, LLP

(57) ABSTRACT

Hybrid tea rose plant having a clear and stable lavender color, strong fragrance and vigorous, upright, well-branched growth.

1 Drawing Sheet

Genus and species: *Rosa hybrida.*
Variety denomination: 'KEIhaburu'.

ORIGIN OF THE INVENTION

The present invention relates to a new and distinct variety of a hybrid tea rose plant named 'KEIhaburu' which was originated by me by crossing the variety 'Madame Violet' (U.S. Plant Pat. No. 6,315), with the variety Silver Star ('KORbido') (Not patented).

BACKGROUND OF THE INVENTION

The primary objective of this breeding was to produce a new rose variety having a clear lavender color, strong fragrance and vigorous plant.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Clear and stable lavender color.
2. Strong fragrance.
3. Vigorous, upright, well-branched growth.

Asexual reproduction of this new variety by cuttings, as performed at Somis, Calif., and at 283 Motoyahagi, Katorishi, Chiba-ken 287-0025 Japan shows that the foregoing and all other characteristics and distinctions come true to form and are established and transmitted through succeeding propagations.

COMPARISON WITH PARENTS AND OTHER VARIETIES

In comparison to seed parent, 'Madame Violet', the peduncle is shorter and straighter. Compared to the pollen parent, 'KORbido', the petals are stronger (thicker) and the stems longer. In comparison to the rose variety 'Madame Violet', 'KEIhaburu' has stems that are 4-5 cm longer and has a more intense fragrance. In comparison to the rose variety 'La Vande' (unpatented), the 'KEIhaburu' variety has a stem length that is 5-10 cm longer and an open bloom flower size of from about 1 cm to 2 cm larger.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—'Madame Violet' (U.S. Plant Pat. No. 6,315).
*Pollen parent.*—Silver Star 'KORbido' (not patented).

FLOWER

Observations were made from January 2006 to July 2006 from plants commencing at one year of age grown in a greenhouse environment at Somis, Calif.

Blooming habit: Continuous.
Bud:
*Size.*—About 30 mm long and 20 mm in diameter when the petals start to unfurl.
*Form.*—The bud form is long, pointed ovoid.
*Color.*—When sepals first divide, bud color is Violet-Blue Group 92B. When half blown, the upper sides of the petals are Violet-Blue Group 92B and the lower sides of the petals are Violet-Blue Group 92B.

*Sepals.*—Color: Upper surface: Green Group N138C. Lower surface: Yellow-Green Group 146B. Length: 20-24 mm. Width: 6-7 mm. Shape: Lanceolate. Surface texture: Hoary. There are three lightly appendaged sepals. There are two unappendaged sepals with hairy edges.

*Receptacle.*—Color: Yellow-Green Group 146C. Shape: Funnel. Size: Medium, about 8 mm long×8 mm wide. Surface: Smooth.

*Peduncle.*—Length: Medium, averaging about 40-50 mm. Surface: Smooth with an occasional gland. Color: Yellow-Green Group 146C. Strength: Stiff, erect.

Bloom:

*Size.*—Medium. Average open diameter is about 80-90 mm.

*Borne.*—Singly and several together in clusters of 5-7 blooms having rounded shape.

*Stems.*—Strength: Strong. Average length is about 40-45 cm with a diameter of 6-7 mm.

*Form.*—When first open: High centered. Permanence: Flattens. Outer petals curl back slightly.

*Petalage.*—Number of petals under normal conditions: 20-25.

*Color.*—The upper sides of the petals are Violet-Blue Group 92B. The reverse sides of the petals are Violet-Blue Group 92B. The base of each petal has a 5 mm×5 mm Yellow-Green Group 154D color spot. The major color on the upper sides of the petals is Violet-Blue Group 92B.

*Variegations.*—On guard petals are occasional Green Group 138D streaks.

*Discoloration.*—The general tonality at the end of the first day: No change. At the end of the third day: No change. Further aging: Fades to Violet-Blue Group 92D in day 5 or 6.

*Fragrance.*—Strong, sweet damask.

Petals:

*Surface texture.*—Smooth.

*Shape.*—Obcordate to orbicular.

*Margin.*—Smooth or entire with some petals notched at the apex. Apex Shape: Rounded or sometimes obcordate. Base Shape: Rounded.

*Form.*—Tips slightly recurved.

*Arrangement.*—Imbricated.

*Petaloids.*—Number: 0 to 1 or 2. Color: Violet-Blue Group 92B. Length: 7-9 mm. Width: 3-5 mm.

*Persistence.*—Petals drop off cleanly before drying.

*Lastingness.*—On the plant: Fair (about 6-7 days). As a cut flower: Fair (about 7-8 days).

Reproductive parts:

*Stamens.*—Number: 70-85. Length: 8-11 mm. Anthers: Length: 3 mm. Color: Yellow-Orange Group 21D. Arrangement: Regular around styles. Filaments: Color: Yellow Group 8D. Length: 5-8 mm. Pollen: Color: Yellow-Orange Group 22A.

*Pistils.*—Number: 45-55. Length: 4-5 mm. Styles: Color: White Group 155C. Length: 3-4 mm. Stigmas: Color: Orange-White Group 159A. Length: 1 mm.

*Hips.*—Color: Yellow-Orange Group 16A. Shape: Round. Size: 25-28 mm diameter.

*Seed.*—10-16/hip. Size: 3-4 mm×3-4 mm. Color: Yellow-Orange Group 22D.

PLANT

*Form.*—Bush.

*Growth.*—Vigorous, upright, branching.

*Age at maturity.*—One year.

*Mature plant.*—Height: 100-120 cm. Width: 60-80 cm.

*Rootstock.*—Own root.

Foliage: Number of leaflets on normal mid-stem leaves: 5.

*Size.*—Medium. About 13 cm long×10 cm wide.

*Quantity.*—Abundant.

*Color.*—New foliage: Upper side: Greyed-Red Group 178A. Lower side: Greyed-Red Group 178A. Old foliage: Upper side: Green Group 139A. Lower side: Yellow-Green Group 147B.

Leaflets:

*Size.*—About 50 mm long×30 mm wide.

*Shape.*—Ovate.

*Base shape.*—Rounded.

*Apex shape.*—Acuminate.

*Texture.*—Leathery, smooth.

*Edge.*—Serrated.

*Serrations.*—Single.

*Petiole.*—Color: Green Group 137D. Length: about 2 mm to 3 mm.

*Petiole rachis.*—Color: Green Group 137D. Underside: Smooth with occasional prickle.

*Auricles.*—None.

*Stipules.*—Length: 9-11 mm; smooth.

*Disease resistance.*—Resistant to rust and susceptible to powdery mildew, downy mildew and blackspot under normal growing conditions.

*Pest resistance.*—None observed.

*Vein color.*—Green Group 137D.

*Venation pattern.*—Reticulate.

Wood:

*New wood.*—Color: Yellow-Green Group 146D. Bark: Smooth.

*Old wood.*—Color: Green Group 137A. Bark: Smooth.

Prickles:

*Quantity.*—On main canes from base: 10-13 per 15 cm of stem. On laterals from main canes: 10-13 per 15 cm of stem.

*Form.*—Hooked downward.

*Length.*—5-6 mm.

*Color when young.*—Greyed-Red Group 178A.

*Color when mature.*—Greyed-Orange Group 165A.

Small prickles:

*Quantity.*—On main stalks: None. On laterals: None.

Winter hardiness: Hardy to Zone 6.

I claim:

1. A new and distinct variety of rose plant of the hybrid tea class, substantially as herein shown and described, characterized particularly by its clear and stable lavender color, strong fragrance and vigorous, upright, well-branched growth.

* * * * *

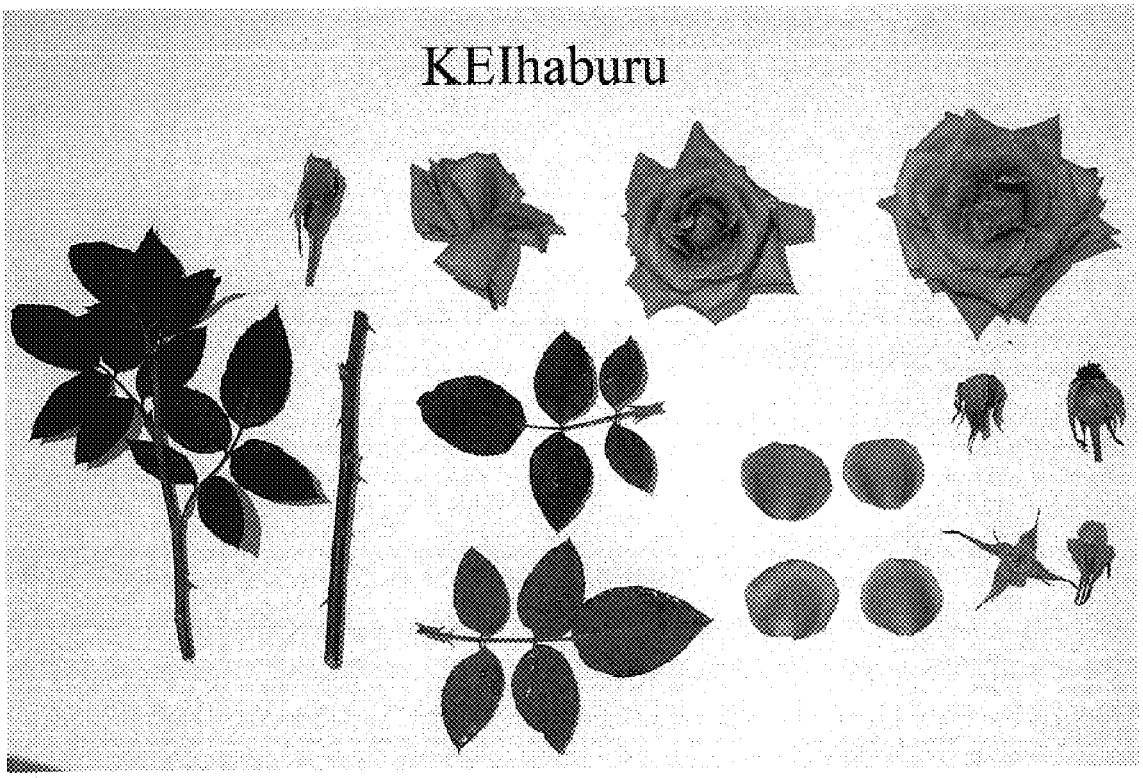
KEIhaburu